United States Patent [19]
Goble et al.

[11] Patent Number: 5,141,520
[45] Date of Patent: Aug. 25, 1992

[54] HARPOON SUTURE ANCHOR

[76] Inventors: E. Marlowe Goble, 850 E. 1200 North; W. Karl Somers, 651 N. 150 West, both of Logan, Utah 84321

[21] Appl. No.: 783,915

[22] Filed: Oct. 29, 1991

[51] Int. Cl.$^5$ .............................................. A61B 17/00
[52] U.S. Cl. .................................... 606/232; 606/60; 606/65; 606/104
[58] Field of Search .................. 606/232, 67, 65, 60, 606/72, 73, 75, 104, 224, 151, 117, 116

[56] References Cited

U.S. PATENT DOCUMENTS

| | | | |
|---|---|---|---|
| 3,512,289 | 5/1970 | Hayes | 606/117 X |
| 4,409,974 | 10/1983 | Freedland | 606/232 |
| 4,497,321 | 2/1985 | Fearing et al. | 606/117 |
| 4,712,550 | 12/1987 | Sinnett | 606/151 |

*Primary Examiner*—Stephen C. Pellegrino
*Assistant Examiner*—Jeffrey A. Schmidt
*Attorney, Agent, or Firm*—M. Reid Russell

[57] ABSTRACT

A harpoon suture anchor and driver, which suture anchor includes a pointed forward harpoon end that is for driving into a bone, the driver for mounting the suture anchor onto one end and is configured to receive a hammer force on its other end, and transmit that force into so as to drive the suture anchor harpoon end into which bone. An end of a suture connects into a cavity of a suture anchor cylindrical body, which cylindrical body fits into a suture anchor mount of the driver that includes a collar for contacting the bone surface limiting suture anchor penetration. Which suture anchor mount is open therethrough as is a driver rod connected thereto, the openings for maintaining the suture fitted therein until the driver and suture anchor mount are pulled therefrom. The invention includes three embodiments of suture anchor harpoon ends: a first embodiment of which is a regular cone that is inturned at a skirt into a wall that extends to the cylindrical body, sloping towards the pointed end, the skirt to flex inwardly as the suture anchor is hammered into a bone; a second embodiment of which is like the first embodiment except spaced arcuate flutes are removed from the regular cone body, leaving spaced body sections in a cross configuration, skirt sections of which body sections to flex inwardly during installation; and a third embodiment of which that is like the second embodiment except that the removed flutes are identically twisted or angled to the longitudinal axis, with the body sections likewise twisted, which twist imparts a rotation to the suture anchor around its longitudinal axes as it is hammered into a bone.

6 Claims, 3 Drawing Sheets

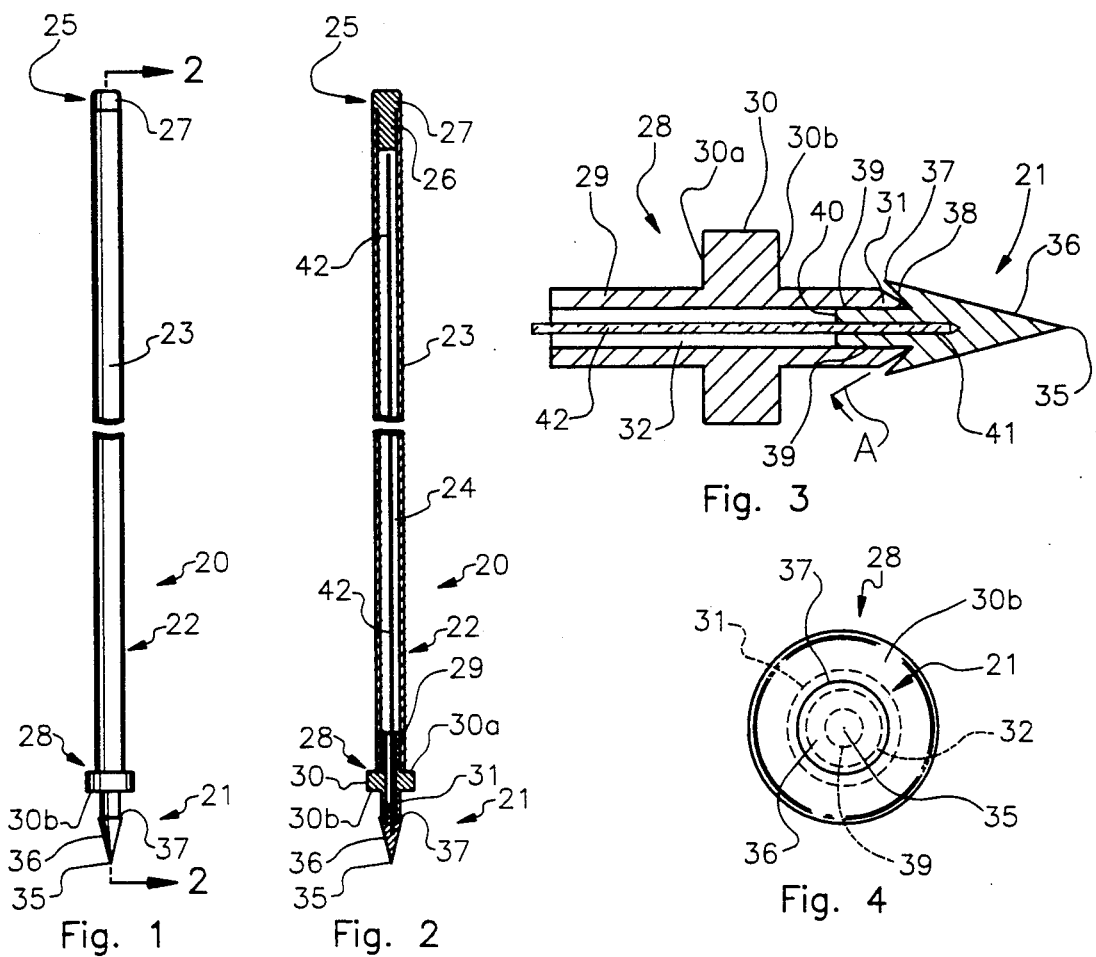

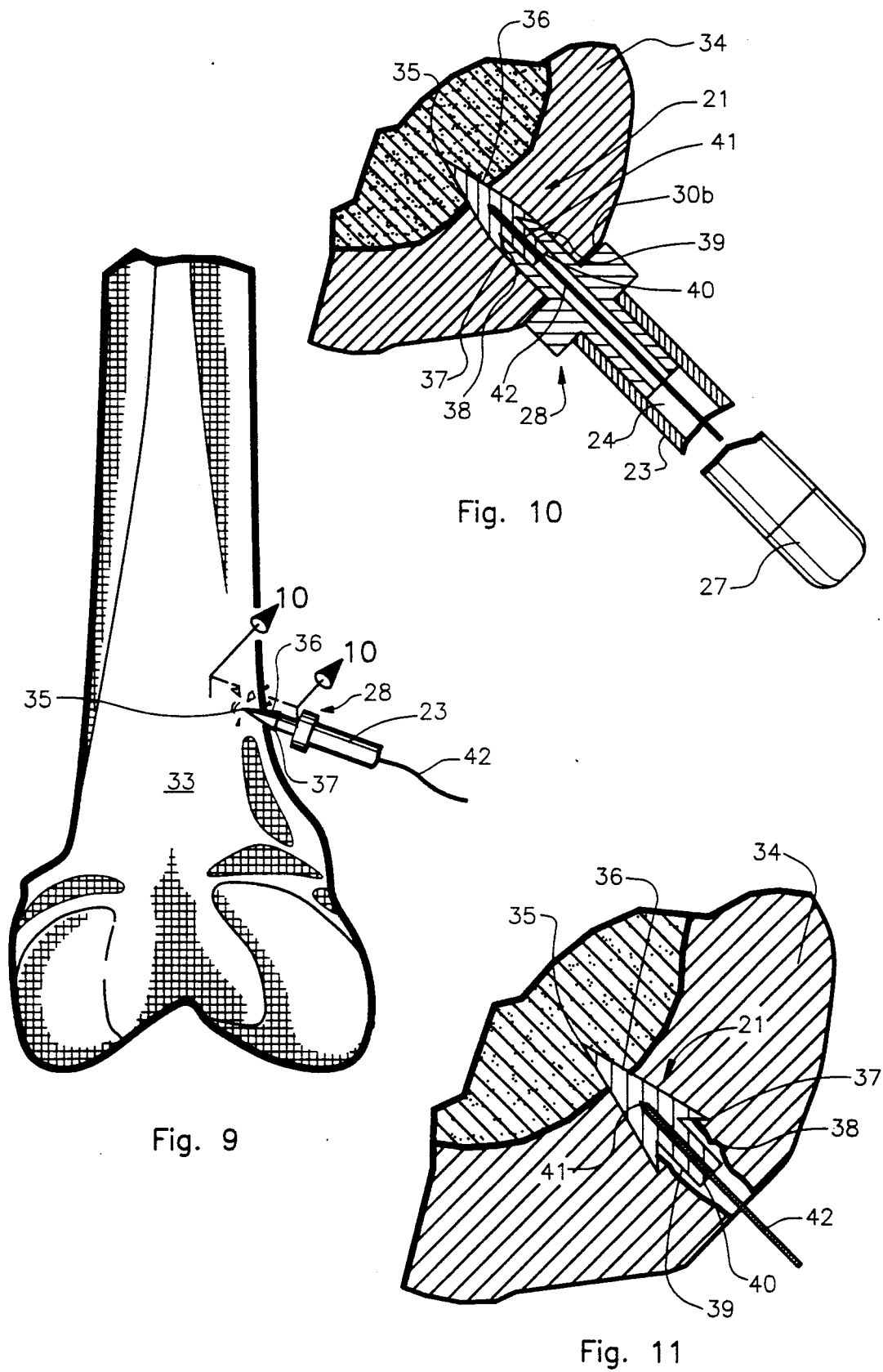

HARPOON SUTURE ANCHOR

BACKGROUND OF THE INVENTION

1. Field of the Invention

This invention relates to suture anchoring devices for use in orthopedic surgical procedures requiring attachment of a suture onto a bone surface.

2. Prior Art

In an orthopedic surgical procedure it is often necessary to attach a suture to a bone surface for use in connecting a tendon or ligament end thereto. Previously, such attachment involved driving a staple into a bone surface with a suture fitted between the staple legs, the staple web fixing the suture to the bone surface. Such procedure was often difficult to perform particularly in areas of limited access and often necessitated a placement of a ligament at less than a most desirable location.

A first patent issued to the present inventors in a Suture Anchor Assembly, U.S. Pat. No. 4,632,100, provided a solution to the problem of fitting a suture onto a bone surface within a confined space. This patent teaches an anchor that is a combination of a drill end with self tapping screw threads formed around the anchor body and provides for attaching a suture end thereto. This arrangement includes a driver that is turned by a conventional drill arrangement turning the stud into a bone. Whereas, the present invention involves a pointed suture anchor that is intended to be driven as by applying a hammer force through a driver for seating which suture anchor in a bone.

Additionally, one of the present inventors was a co-inventor of a suture anchor device, in a patent entitled, Suture Anchor System, U.S. Pat. No. 4,738,255, which arrangement provides for drilling an outwardly tapering hole into a bone and fitting and expanding an acorn shaped anchored therein that includes a suture end fixed thereto. Which arrangement is unlike the present invention that does not involve drilling into a bone surface prior to driving the anchor therein. Similar to the above and distinct from the present invention, an anchor device for installation in a prepared bone cavity is also shown in a U.S. Pat. No. 4,409,974, that includes a bone seating arrangement that is unlike the present invention in its design and functioning. A screw and washer combination for clamping a ligament against a bone surface is shown in a U.S. Pat. No. 4,988,351, that is structurally and functionally unlike the present invention.

The above are examples of anchor devices for turning into a bone or for fitting into a hole formed into a bone. Unlike these and like devices, the present invention is arranged to be driven into a bone and is configured for locking therein against an anticipated tensile force as could be applied to the connected suture. Of course, a number of devices, including a staple, have been utilized for securing a ligament, suture, or the like, onto a bone surface that have involved applying a hammer force to such device so as to drive it into a bone surface. Another patent by the present inventors in a Channel Ligament Clamp, U.S. Pat. No. 4,960,420, is an example of a ligament clamp with spaced pins for driving into a bone surface, clamping a ligament thereto. Additional to the above set out clamp arrangement of the present inventors, examples of other clamps for utilization in the performance of a medical procedure are shown in U.S. Pat. Nos. 4,146,022, 4,592,346, and 4,793,335, and examples of staple and pin type devices for use in the practice of a medical procedure are shown in U.S. Pat. Nos. 4,047,524, 4,263,903, 4,278,091, 4,400,833, 4,414,967, 4,438,769, 4,456,006, 4,711,234, 4,759,765 and U.K. Patent, No. GB 2,118,662 none of which staple and pin arrangements have involved a harpoon pointed anchor like that of the present invention and are functionally dissimilar therefrom.

SUMMARY OF THE INVENTION

It is a principal object of the present invention to provide a harpoon suture anchor and driver where a surgeon, applying a hammer force to the driver end, can permanently seat the suture anchor harpoon pointed end in a bone surface, which driver is then pulled off from the suture anchor leaving a suture extending therefrom.

Another object of the present invention is to provide a for mounting a suture anchor in a bone material where only limited access is available to the anchor site on the bone surface.

Another object of the present invention is to provide a suture anchor that can be installed in a bone that does not require a prior site preparation.

Another object of the present invention is to provide a suture anchor that includes, as a harpoon pointed end, a cone that slopes outwardly from a pointed cone apex into a skirt, the pointed apex to penetrate a bone surface when a hammer force is applied through the driver, the sloping surface of which harpoon end pushing away the bone materials as the suture anchor is driven into that bone material.

Another object of the present invention is to provide a suture anchor cone end and driver forward end that are arranged to allow the cone skirt to flex inwardly as the suture anchor is driven into the bone surface, that skirt to flex outwardly, into the bone material, with the removal of the driving force.

Still another object of the present invention is to provide a suture anchor where the harpoon end is fluted at intervals therearound from apex to skirt, leaving body sections therebetween.

Still another object of the present invention is to provide a spiral to each flute and adjacent body section that causes a rotation to which suture anchor as it is forced into the bone materials, which rotation moves the body sections skirt edges out from alignment with the path of suture anchor entry, aligning the skirt section edges with less disrupted bone materials to anchor in, providing a suture anchor with a greater pull out strength.

Still another object of the present invention is to provide a suture anchor with a harpoon end that can be manufactures from a metal or hard plastic suitable for body implantation that is easily and permanently seated in a bone, and includes a suture attached to that anchor that is for use for connecting a ligament, or the like, to the bone surface in a practice of an orthopedic surgical procedure.

The present invention is a harpoon suture anchor that includes a cylindrical body that is open longitudinally at one end and receives a suture end fitted and secured therein. The opposite end of which cylindrical body mounts, as the harpoon end, a cone shaped segment having a pointed apex and slopes outwardly therefrom to a skirt that is inturned into a wall that slopes towards the apex end, intersecting the body surface. The cone shaped harpoon end, in one embodiment, is a regular cone, the skirt edge thereof to flex towards the cylindrical body when urged through a bone surface, and will return to its original attitude when seated in the bone material. A second embodiment of which harpoon end is also formed as a regular cone, but which cone is fluted at intervals therearound from its apex to skirt, leaving body and skirt sections, from which skirt sections walls slope towards the apex end and intersect the body surface. In a third embodiment, the flutes, body and skirt sections are identically spiraled or curved from apex to skirt edge. Which spiral or curve imparts a rotation to the suture anchor as it is urged into bone material, offsetting the skirt sections from the path of entry of which suture anchor, which skirt sections are accordingly positioned opposite to bone materials that have been minimally disturbed by suture anchor passage and therefor provide an improvement in pull out strength.

A driver is provided for imparting a hammer force into which harpoon suture anchor to drive the harpoon end into a bone cortex. The driver is a cylinder or rod that is open longitudinally therethrough to receive and maintain the suture a suture anchor mount that is also open longitudinally and receives the suture anchor end therein. The suture anchor mount has a sloping forward end that will travel beneath the sloping suture anchor wall, the slope of which suture anchor mount end is angled to provide a space or gap between the wall suture anchor mount end, which space or gap allows the suture anchor skirt to flex toward the suture anchor cylindrical body during installation. Additionally the suture anchor mount incudes a collar arranged therearound located back from the forward or suture anchor engaging end, which collar forward face provides a stop, for contacting the bone surface, limiting the depth of suture anchor penetration. The driver rear end preferably includes a plug for fitting in the longitudinal passage, closing off that passage and containing the suture therein, which plug is to be hammered on by a surgeon driving the suture anchor through a bone surface and into the bone materials.

DESCRIPTION OF THE DRAWINGS

In the drawings is shown that which is presently regarded as the best mode for carrying out the invention:

FIG. 1 is a profile side elevation view of a harpoon suture anchor and driver of the present invention;

FIG. 2 is a profile sectional view taken along the line 2—2 of FIG. 1;

FIG. 3 is an enlarged profile sectional view of a first embodiment of a harpoon suture anchor of the present invention shown mounted on the end of a suture anchor mount and includes an end of a suture secured thereto;

FIG. 4 is a forward end view of the harpoon suture anchor of FIG. 3 showing, in broken lines, the suture anchor interior and the suture anchor mount forward or suture anchor mounting end;

FIG. 5 is a view like FIG. 3, only showing another or second embodiment of the harpoon suture anchor and suture anchor mount of the present invention;

FIG. 6 is a view like FIG. 4, only showing a forward end view of the harpoon suture anchor of FIG. 5;

FIG. 7 is a view like those of FIGS. 3 and 5, only showing still another or third embodiment of the harpoon suture anchor and suture anchor mount of the present invention;

FIG. 8 is a view like those of FIGS. 4 and 6, only showing a forward end view of the harpoon suture anchor of FIG. 7;

FIG. 9 is a side elevation view of a section of bone showing the harpoon suture anchor of FIGS. 1 through 4, mounted on the forward end of a suture anchor mount and driver illustrating a hammer force being applied through the driver for hammering the suture anchor into the bone cortex;

FIG. 10 is an enlarged top plan sectional view of the harpoon suture anchor, suture anchor mount and driver taken along the line 10—10 of FIG. 9;

FIG. 11 is a view like that of FIG. 10 with the suture anchor mount removed and showing the harpoon suture anchor seated in the bone cortex;

DETAILED DESCRIPTION

Figure 12:
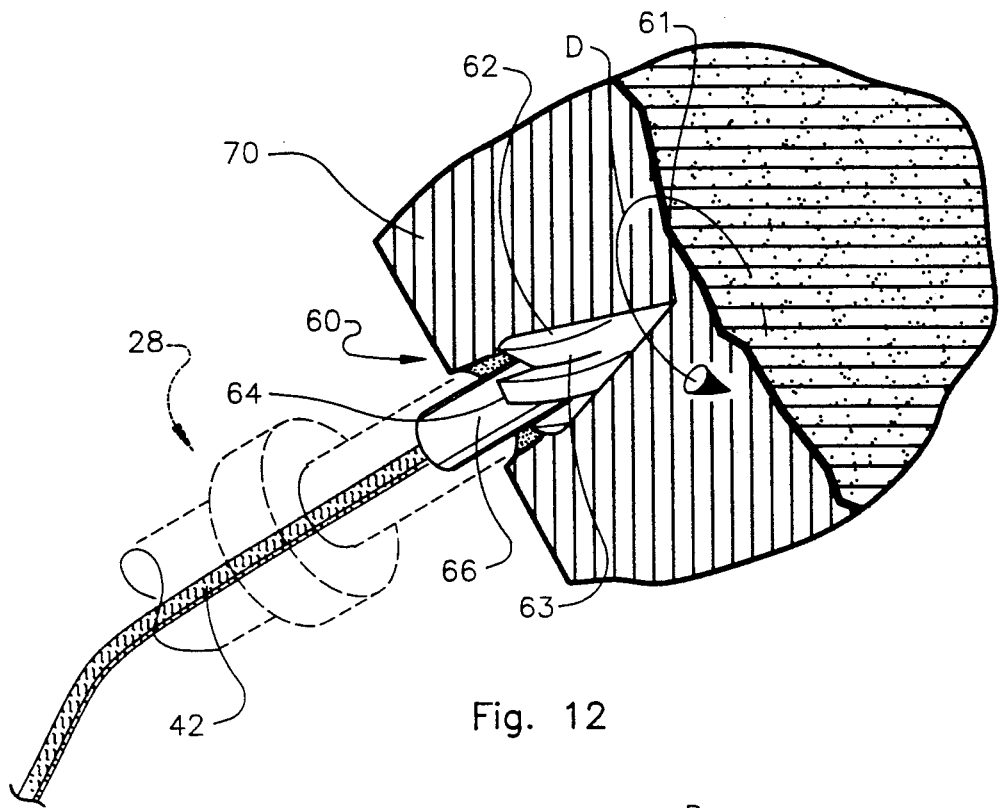
FIG. 12 is an enlarged perspective view of a section of bone showing the harpoon suture anchor of FIGS. 7 and 8 mounted onto the end of the suture anchor mount, shown in broken lines, being driven through the bone surface and into the bone cortex, a curved arrow indicating that the suture anchor is turning as it is urged into which bone.

A harpoon suture anchor and driver 20 of the present invention is shown in side elevation in FIG. 1, and as a side elevation sectional view in FIG. 2. A harpoon suture anchor 21, hereinafter referred to as suture anchor, is shown fitted onto an end of a driver 22, that is shown as consisting of a rod 23 having a center longitudinal opening 24 therethrough with a suture anchor mount 28 fitted to the rod end whereon the suture anchor 21 is mounted. The driver 22 is capped at its end opposite to the suture anchor mount 28 by an insert head 25. Which insert head is stepped at a right angle outwardly from a body 26 to a broad head 27, which body 26, as shown best in FIG. 2, is for insertion into the longitudinal opening 24. The broad head 27 end is to be struck by a surgeon, as with a hammer, to impart a hammer force through driver 22 and into the suture anchor 21, as set out hereinbelow.

The suture anchor mount 28, as shown in FIGS. 3, 5 and 7, is useful with each suture anchor embodiment of the present invention. As shown therein, the suture anchor mount 28 includes a cylindrical body 29 for fitting, as shown in FIG. 2, into the open end of rod 23, opposite to the insert head 25. The cylindrical body 29 is slide into which rod longitudinal opening to where the rod end butts against an upstanding face 30a of a collar 30. A hammer force applied to the insert head 25 is thereby transmitted through the rod 23 and into the collar 30, wherefrom that force acts through the suture anchor mount 28 and into a suture anchor mounted thereto. The collar 30 is preferably cylindrical, having rear and forward walls 30a and 30b, respectively, that are each flat and are at approximately right angles to the cylindrical body 29. The forward of which collar wall 30b is to act as a stop, as shown best in FIG. 10, limiting the depth of penetration of the suture anchor into a bone, as set out herein below.

A forward or suture anchor mounting end 31 of the suture anchor mount 28 is shown in FIGS. 3, 5 and 7, as sloped or tapered. The angle A of which slope or taper, as shown in FIG. 3 is preferably approximately thirty (30°) degrees from the horizontal, plus or minus fifteen (15°) degrees. This slope allows an undercut surface of the suture anchor, as discussed in detail hereinbelow, to fitted over which suture anchor mount end 31, leaving a space therebetween. In FIG. 5 angle B is illustrated as the suture anchor undercut surface formed at approximately a forty-five (45°) degree angle to the horizontal, plus or minus fifteen (15°) degrees. In FIG. 7 the space between which suture anchor mounting end 31 and the suture anchor undercut surface or wall is show as angle C, which angle C is the product of a subtraction of angle A from angle B, or, as shown, approximately fifteen (15°) degrees, plus or minus five (5°) degrees. The space, shown as angle C, as set out hereinbelow, is to allow the suture anchor skirt to flex towards the suture anchor mount body 29 when that suture anchor is hammered into a bone, and accordingly angles A and B must be selected within their range of angles to produce an angle C of at least ten (10°) degrees.

The suture anchor mount 28 is for receiving the suture anchor 21 of FIGS. 1 through 4, and mounts also the suture anchor embodiments of FIGS. 5 through 8. Mount 28 includes a center longitudinal passage 32 formed therethrough that aligns with the rod 23 longitudinal opening 24 to receive a suture of the suture anchor fitted therein, as set out hereinbelow.

A first embodiment of suture anchor 21 is shown best in FIGS. 3 and 4, and is shown in FIGS. 9 through 411, being hammered into a bone 33 for seating in the bone cortex 34. The suture anchor 21 incorporates a pointed forward end 35 that, as shown in FIG. 9, is for penetrating a bone 33 surface. From the pointed end 35, the suture anchor harpoon end body 36 tapers uniformly outwardly, as a regular cone, terminating in a skirt 37. At skirt 37 the harpoon end is then turned inwardly into a flat wall 38 that slopes towards the pointed end 35 and intersects a cylindrical body 39 of which suture anchor. A rear end 40 of which suture anchor cylindrical body 39 includes a center longitudinal hole 41 formed therein for receiving and securing an end of a suture 42. Which suture 42, as shown, extends from the suture anchor, passes through the suture anchor mount 28 center longitudinal passage 32 and is contained within the driver 22 center longitudinal opening 24, as illustrated in FIG. 2. Which suture 42, as shown in FIG. 11, extends from the suture anchor end 40 after the driver 22 and suture anchor mount 28 are pulled therefrom.

In practice, as illustrated in FIG. 10, the suture anchor is driven through a bone 33 surface and into the bone cortex 34. Of course, depending upon the thickness of which cortex, for some applications the suture anchor skirt 37 will travel beyond and seat in the bone material adjacent to which cortex inner surface. The limit of insertion of which suture anchor is governed by the collar 30 forward face 30b that contacts the bone surface, limiting bone penetration. Shown in FIG. 10, the suture anchor 21, mounted to the suture anchor mount 28, is driven into the bone cortex to where the collar face 30b engages the bone 33 surface. In that penetration the suture anchor skirt 37 is flexed toward the surface of suture anchor cylindrical body 39, which flexure is allowed by the gap between which skirt undersurface wall 38 and the surface of the suture anchor mount sloping forward end 31, shown as angle C. That flexure continues until the suture anchor is fully installed, whereat the hammer force is discontinued and the skirt 37 flexes outwardly. The skirt thereby travels into the bone cortex materials that have sagged back into the passage formed by passage of the suture anchor and into the bone materials that have not been affected by that passage, as shown in FIG. 11. So arranged, a suture anchor seating is purchased by the skirt 37 flexing into the bone materials, which purchase, as set out in test date hereinbelow, is greater than a tensile force as could reasonably be expected to be applied through suture 42.

Another or second embodiment of a harpoon suture anchor 50, hereinafter referred to as suture anchor, is shown in FIGS. 5 and 6. Suture anchor 50 is for mounting to the described suture anchor mount 28 and driver rod 22 for driving into a bone 33 as described above, and the installation of the suture anchor 50 should be taken as being like that of the above described suture anchor 21. Distinct therefrom, however, rather than the regular cone body 36 of the suture anchor 21, from a pointed end 51 of suture anchor 50 the suture anchor body is fluted or slotted at 53 at spaced intervals therearound forming body sections 52. As shown, each flute or slot 53 is approximately thirty (30°) degrees of arc outwardly of a cylindrical body 56.

Shown best in the end view of FIG. 6, the body sections 52 form a cross that slopes outwardly to skirt sections 54. Which skirt sections are each inturned into wall sections 55 that slope toward the pointed end 51 and intersect the cylindrical body 56. The suture anchor cylindrical body 56 has a flat rear face 57 and is for installation into the suture anchor mount 28 longitudinal passage 32. A center longitudinal hole 58 is formed into which cylindrical body flat rear face 57 for receiving and securing an end of suture 42 therein. The procedure for installing suture anchor 50 into a bone is essentially identical to that described with respect to the installation of suture anchor 21. In the installation of suture anchor 50, however, the suture anchor body sections 52 as they present a lesser area tend to more readily flex inwardly at their skirt sections than does the suture anchor 21 skirt, thereby producing less disruption to the bone material wherethrough the suture anchor is hammered. In that passage bone materials are displaced by the pointed end 51 and flow through the flutes or spaces 53, alongside the body sections 52, producing less bone disruption than occurs with the cone shaped body 36 of suture anchor 21. The displaced bone materials flow thereby tends to be more dense as it fills in behind the suture anchor 51 than is present following the suture anchor 21, tending to provide denser bone materials between the suture anchor skirt sections 54 resisting suture anchor withdrawal, and accordingly purchases a pull out strength that is much greater than can be anticipated to be applied to the suture 42.

In pull out tests of suture anchor 50 that involved seating the suture anchor in clear pine blocks, all of which were cut from the same board, for seven tests, the pull out strength in pounds for each test, was found to be: 46.2; 47.5; 48.7; 45.0; 40.0; 37.0; and 48.7. For this series of tests, suture anchor 50 demonstrated an average pullout strength of 44.7 pounds, with a high of 48.7 pounds and a low of 37.0 pounds, which average pull out strength is far greater than an anticipated tensile force as a suture 42 could be expected to be subjected to. It is anticipated that, based upon the above set out differences between suture anchors 21 and 50 functioning, suture anchor 21 will exhibit a slightly smaller pull out strength than that exhibited by suture anchor 50. Which pull out strength of suture anchor 21 is accordingly estimated to be approximately 42.0 pounds plus or minus five (5) pounds.

Figure 13:
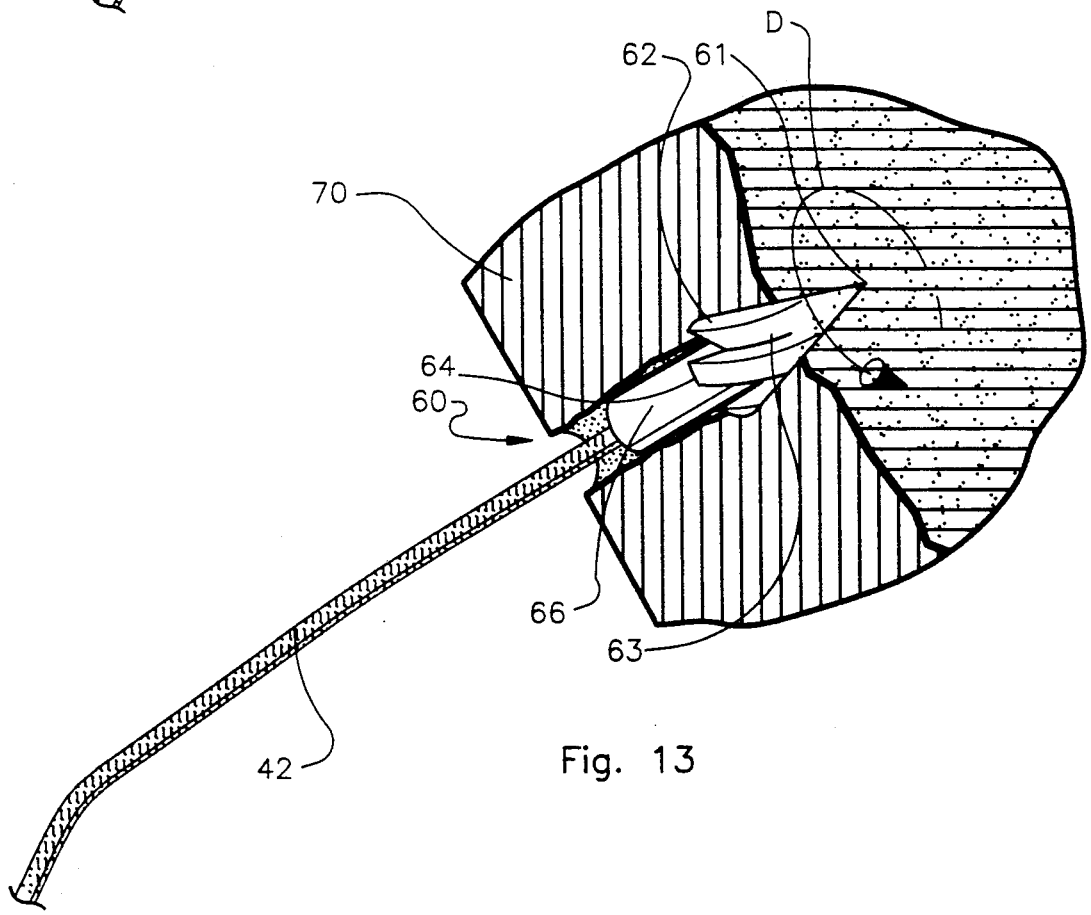
FIG. 13 is a view like that of FIG. 12 showing the suture anchor seated in the bone cortex.

Still another or third embodiment of a harpoon suture anchor 60, hereinafter referred to as suture anchor, is shown in the views of FIGS. 7 and 8, and is shown installed in FIGS. 12 and 13. Suture anchor 60, like suture anchor 50, has a pointed forward end 61 with spaced outwardly tapering body sections 62 extending rearwardly therefrom that terminate in skirt sections 64, and with flutes or slots 63 formed between which body sections. The suture anchor 60, like suture anchor 50, from skirt sections 64, also includes inturned forwardly sloping wall sections 65 that intersect a cylindrical body 66. Which cylindrical body 66 has a flat rear end 67 wherein a center longitudinal cavity 68 is formed for receiving and securing therein an end of suture 42.

Distinct from suture anchor 50, the body sections 62 and adjacent flutes or slots 63 therebetween of suture anchor 60 are formed to have an identical spiral of approximately fifteen (15) degrees of arc. During installation, as the suture anchor is forced into a bone cortex 70, as shown in FIG. 12, the bone materials passing through the flutes or slots 63 imparting a twist to the suture anchor 60, illustrated as curved arrow D in FIGS. 12 and 13. Thereby, the skirt sections 64 of which suture anchor 60 are displaced out of the suture anchor entry path to be essentially aligned with minimally disturbed bone materials that lie on a straight line from which skirt section to the bone surface, as shown in FIG. 13. Accordingly, a tensile force applied through suture 42 tends to outwardly flex the skirts sections 64 into which essentially undisturbed bone materials, providing a better anchor support than is provided to the skirt sections 54 of seated suture anchor 50. In pull out tests performed on suture anchor 60 like those performed on suture anchor 50, as set out above, the suture anchor 60 pulled out of clear pine blocks at; 46.0; 47.5; 51.8; 47.5; 50.0; and 54.3 pounds, respectively, for an average pull out strength of 49.5 pounds. Which average pull out strength is therefor 4.8 pounds greater for suture anchor 60 than suture anchor 50. Accordingly, the average pull out strength of suture anchor 60 is also far greater than an anticipated tensile force as could be expected to be applied through suture 42.

As indicated above, all the suture anchor embodiments are for use with driver 21 and suture anchor mount 28 for seating in a bone, with the attached suture 42 extending therefrom. Which seating involves applying a hammer force through the driver 21 to force the suture anchor pointed end through the bone surface, spreading the bone cortex materials as the suture anchor enters, with those materials flowing back into the suture anchor entry path, and the suture anchor skirt or skirt sections flexing into and anchoring into which bone materials. A hard material is therefor required for the construction of which suture anchor to provide an appropriate pointed end. Which material may to a metal such as 316 stainless steel, suitable for remaining in which bone, or may be a hard plastic material, such as DELRIN TM, that will be absorbed into the body over time.

While preferred embodiments of a harpoon suture and anchor and driver of the present invention have been shown and described herein, it should be understood that the present disclosure is made by way of example only and that variations are possible without departing from the subject mater and reasonable equivalency thereof, coming within the scope of the following claims, which claims we regard as our invention.

We claim:

1. A harpoon suture anchor comprising, a cylindrical body that is open on one end and secures a suture end therein; a harpoon end means mounted to said cylindrical body opposite to said open end, which harpoon end means is a regular cone having a pointed end and is tapered outwardly therefrom into a skirt that is inturned into a wall that intersects said cylindrical body surface, sloping toward said pointed end, and which said regular cone is fluted at spaced intervals therearound from point to skirt, said flutes each identically angled from the cylindrical body longitudinal axis, forming spaced body and skirt sections extending outwardly from around the cylindrical body surface; and driver means for urging said harpoon suture anchor end means into a bone.

2. A harpoon suture anchor as recited in claim 1, wherein the harpoon end means skirt allows flexure of said skirt sections towards the cylindrical body surface during harpoon suture anchor installation.

3. A harpoon suture anchor as recited in claim 1 wherein each flute is angled at approximately fifteen (15) degrees.

4. A harpoon suture anchor as recited in claim 1, wherein the driver means comprises a tube with proximal and distal ends that is open longitudinally therethrough, and a solid cylindrical rod, for fitting in the proximal tube end, that is stepped inwardly at one end to fit into the proximal tube end, said solid cylindrical rod includes a flat end, opposite said stepped end for striking, as with a hammer; and a suture anchor mount, having one end for fitting in said distal tube end mounts and the harpoon suture anchor cylindrical body to its opposite end, said suture anchor mount includes a cylindrical collar with essentially parallel opposite faces therearound for contacting, on one face, said distal tube end and, with the opposite cylindrical collar face for limiting harpoon suture anchor penetration.

5. A harpoon suture anchor recited in claim 4, wherein the suture anchor mount is tapered at a forward end that is to engage the junction of the suture anchor sloping wall, the suture anchor mount taper is at a lesser angle, relative to the suture anchor mount longitudinal axis, than the angle the suture anchor sloping wall is to the cylindrical body longitudinal axis, proving a space therebetween.

6. A harpoon suture anchor as recited in claim 5, wherein the slope of the suture anchor mount taper is thirty (30) degrees, plus or minus fifteen (15) degrees, and the slope of the suture anchor sloping wall is forty-five (45) degrees, plus or minus fifteen (15) degrees, with a minimum angle of ten (10) degrees between the suture anchor mount taper and the suture anchor sloping wall.

* * * * *